[19] United States Patent
Pollard

[11] 3,960,154
[45] June 1, 1976

[54] NOVEL HAIR GROOMING COMPOSITION, AND A METHOD AND AN INSTRUMENT EMPLOYING THE SAME

[76] Inventor: Eula Mae Pollard, Rte. 6, Box 713-A, Hot Springs, Ark. 71901

[22] Filed: Sept. 16, 1975

[21] Appl. No.: 613,893

[52] U.S. Cl. .................................. 132/9; 132/112
[51] Int. Cl.² ........................................... A45D 1/00
[58] Field of Search ........................... 132/112, 9, 7

[56]  References Cited
UNITED STATES PATENTS

| | | | |
|---|---|---|---|
| 3,424,176 | 1/1969 | Hale | 132/112 |
| 3,640,288 | 2/1972 | Spanel | 132/9 |
| 3,683,942 | 8/1972 | McKay | 132/112 |
| 3,828,802 | 8/1974 | Spanel | 132/9 |

Primary Examiner—G.E. McNeill
Attorney, Agent, or Firm—L. S. Van Landingham, Jr.

[57] ABSTRACT

A hair grooming composition is provided which consists essentially of about 5–15% by volume of bees wax and about 95–85% by volume of paraffin wax. The composition is preferably in the form of a reinforced body which resists damage or breakage when applying to the hair. An instrument for grooming the hair having a handle, such as a hair brush or comb, is also provided wherein a coherent body of the hair grooming composition is applied to the handle. The handle is grasped by the hand when grooming the hair with the instrument thereby warming the composition prior to applying a thin coating thereof to the hair. A method of grooming the hair is also provided which employs the hair grooming composition and/or instrument of the invention.

10 Claims, 11 Drawing Figures

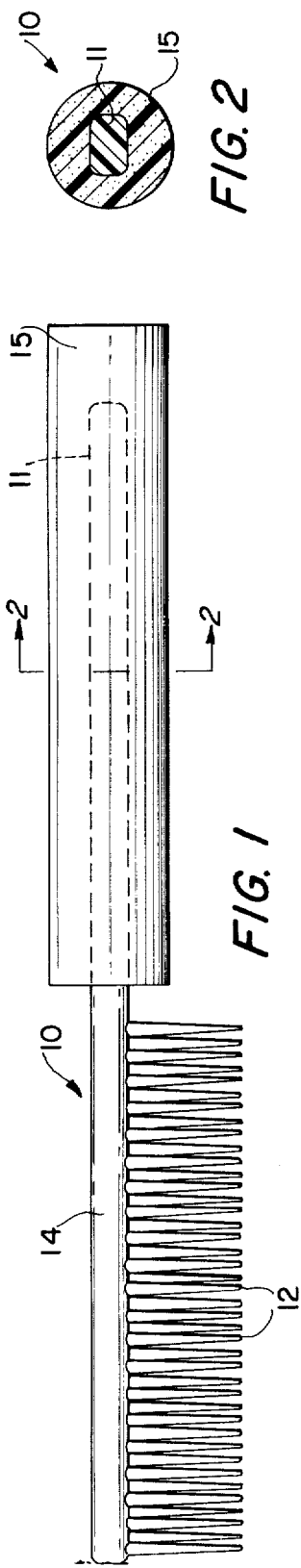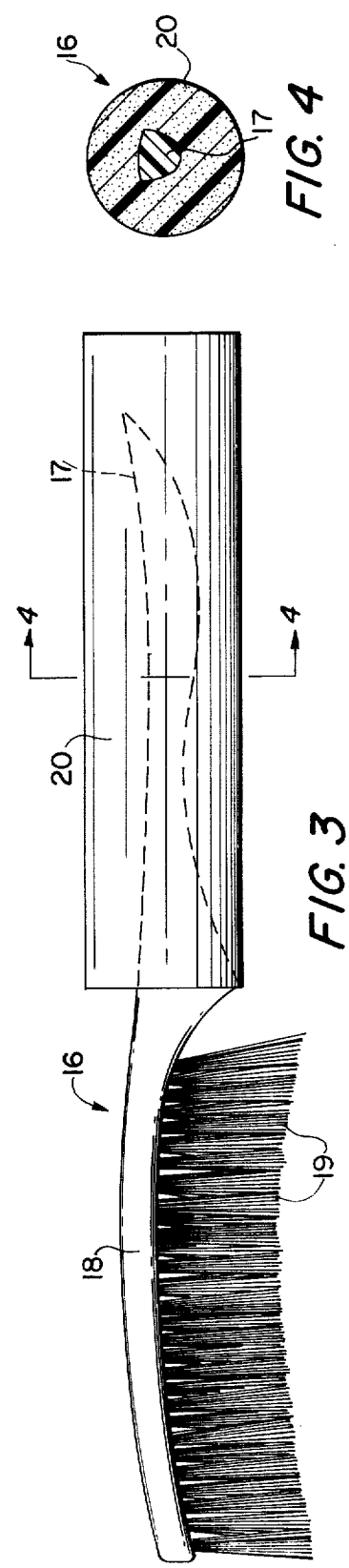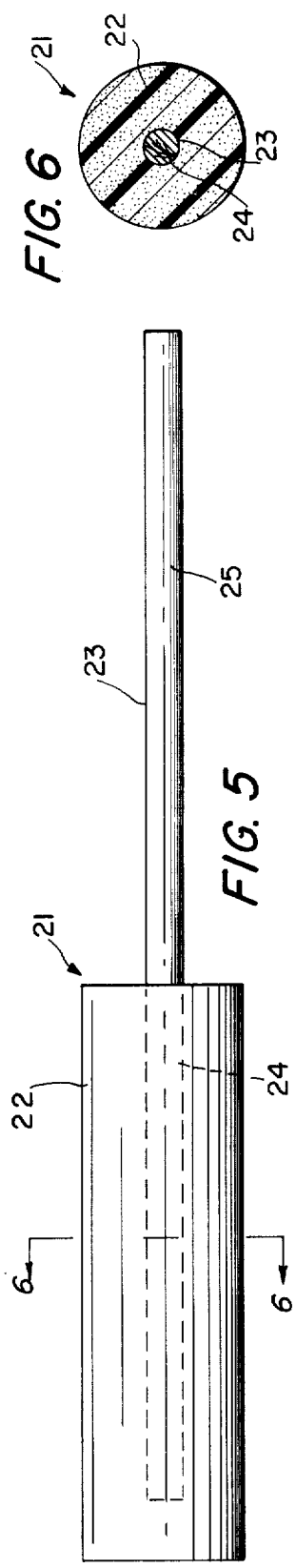

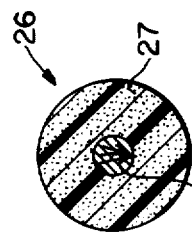
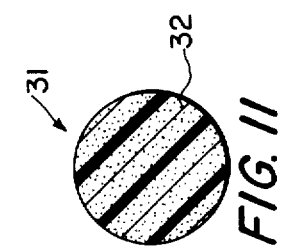
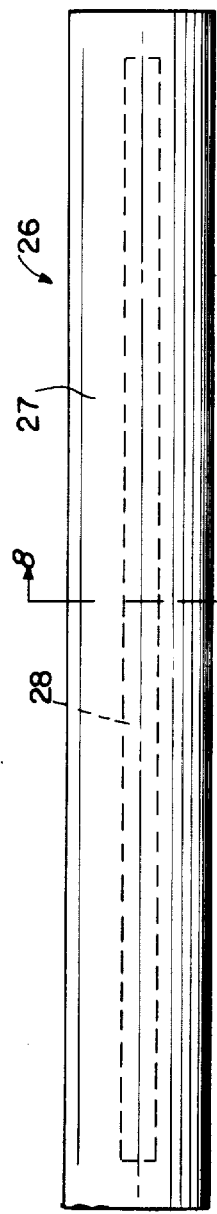
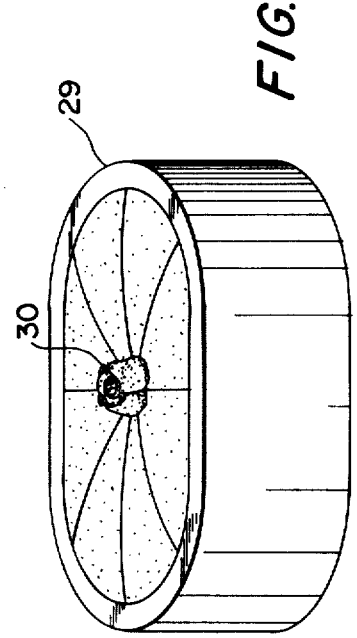
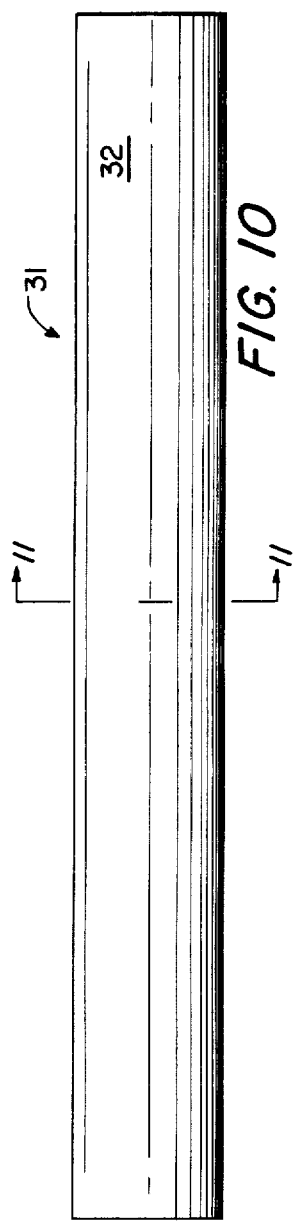

NOVEL HAIR GROOMING COMPOSITION, AND A METHOD AND AN INSTRUMENT EMPLOYING THE SAME

THE BACKGROUND OF THE INVENTION

1. The Field of the Invention

The present invention broadly relates to a novel hair grooming composition. The invention is also concerned with a novel method and an improved instrument employing the aforementioned hair grooming composition.

2. The Prior Art

A wide variety of hair grooming compositions have been proposed heretofore. The compositions are usually in the form of liquids or semi-solids and contain a relatively large number of ingredients. The ingredients may include bees wax or paraffin wax, but in such instances the prior art compositions contain additional modifying ingredients which change the basic properties of the bees wax and paraffin wax.

Many of the prior art hair grooming compositions could not be conventiently applied to the hair in the form of a thin uniform film of controlled thickness. The prior art hair grooming compositions also, often made the hair greasy, or caused the individual strands to stick together, or otherwise resulted in an unsightly appearance and especially when applied in excess. In instances where an insufficient amount of the hair grooming composition was applied, then it was ineffective for the intended purpose.

Many of the prior art hair grooming compositions also were not available in a convenient solid form which had sufficient strength for applying a controlled uniform film thereof to the hair without damaging or breaking the same.

Hair grooming insturments such as combs and hair brushes have been used heretofore for applying hair grooming compositions. However, when the prior art instruments were used for this purpose they employed either the brush bristles or the comb teeth for application of the hair grooming compositions as distinguished from the handle. As a result, it was not convenient heretofore to warm the hair grooming composition with the hand prior to application. Thus, the warmth of the hand was not generally used heretofore for warming the prior art hair grooming compositions.

The aforementioned and other disadvantages of the prior art hair grooming compositions and instruments, and also the methods of using the same, were well known to those skilled in the art. Nevertheless, in spite of the great and long existing need for improvements therein, such improvements were not available in an entirely satisfactory form prior to the present invention.

THE SUMMARY OF THE INVENTION INCLUDING CERTAIN OBJECTS THEREOF

The present invention provides an entirely satisfactory novel solid composition for use in grooming the hair. The composition consists essentially of bees wax and paraffin wax in carefully controlled critical amounts which assure the necessary consistency for application to the hair in the form of a thin, uniform, non-greasy film. The resultant film adds a maximum amount of body to the hair and protects and preserves the hair without any adverse effects in the form of free flowing individual strands. Thus, when applying the hair grooming composition by the method of the invention, an optimum amount of the hair grooming composition is applied automatically due to the critical physical properties thereof.

The invention also provides a reinforced body or shape of the hair grooming composition which aids in the application thereof to the hair without damage or breakage. The reinforced body or shape is easy to use and apply in the desired quantity.

The presence of the hair grooming composition on the handles of hair grooming instruments such a combs and hair brushes has a number of beneficial effects. For example, the hair grooming composition is even easier to apply to the hair in the aforementioned critical amounts when it has first been warmed slightly. The warmth of the hand is sufficient for this purpose. Therefore, when a coherent body of the hair grooming composition is present on the handle of a hair grooming instrument, the composition is warmed by the hand and may thereafter be applied with even more pronounced beneficial effects.

THE OBJECTS OF THE INVENTION

It is an object of the present invention to provide a novel solid composition for use in grooming the hair which consists essentially of bees wax and paraffin wax.

It is a further object to provide a reinforced body or shape of a hair grooming composition prepared from the above ingredients which may be easily applied to the hair while maintaining the general integrity thereof.

It is still a further object to provide an instrument for grooming the hair which consists essentially of a body or shape of the aforementioned solid hair grooming composition and a reinforcing means therefor.

It is still a further object to provide an instrument for grooming the hair having a handle whereby the aforementioned hair grooming composition may be applied to the handle and warmed by the hand while grooming the hair with the instrument prior to applying the same.

It is still a further object to provide a novel method for applying the aforementioned hair grooming composition which employes the reinforced solid hair grooming composition of the invention and/or the hair grooming instrument of the invention.

The accompanying illustrative drawings, the specific examples, and the detailed description of the preferred variants and embodiments of the method, apparatus and composition of the invention may be referred to for still additional objects and a more complete and comprehensive understanding of the invention.

A BRIEF DESCRIPTION OF THE ACCOMPANYING DRAWINGS

The present invention will be described hereinafter in greater particularity with reference to the embodiments thereof illustrated in the accompanying drawings, wherein:

FIG. 1 is a view of a comb constructed in accordance with the principles of the present invention;

FIG. 2 is a sectional view taken along the lines 2—2 of FIG. 1;

FIG. 2 is a view of a hair brush constructed in accordance with the principles of the present invention;

FIG. 4 is a cross-sectional view taken along the lines 4—4 of FIG. 3;

FIG. 5 is a view of an improved instrument for applying the hair grooming composition of the present invention to hair;

FIG. 6 is a cross-sectional view taken along the lines 6—6 of FIG. 5;

FIGS. 7 and 10 are views of elongated reinforced and unreinforced rods or sticks, respectively, of the hair grooming composition of the present invention;

FIGS. 8 and 11 are cross-sectional views taken along the lines 8—8 and 11—11 of FIGS. 7 and 10, respectively, and FIG. 9 is a view of an unreinforced bar of the hair grooming composition of the invention.

THE DETAILED DESCRIPTION OF THE PRESENT INVENTION INCLUDING PREFERRED VARIANTS AND EMBODIMENTS THEREOF

The hair grooming composition of the present invention consists essentially of about 5–15% by volume of bees wax and about 95–85% by volume of paraffin wax. In a preferred variant, the composition consists essentially of about 10% by volume of bees wax and about 90% by volume of paraffin wax.

When desired, the hair grooming composition also may contain a perfume or coloring agent in small effective amounts such as are conventional in this art. In most instances it is usually preferred that perfumes and colorants be omitted so as to provide a hair grooming composition which contains only bees wax and paraffin wax as naturally occurring ingredients. In instances where a perfume or colorant is used, then naturally occurring perfumes and colorants of the prior art are preferred. Examples of naturally occurring perfumes include the essential oils such as natural lavender oil, thyme oil, bergamot oil, essence of basil, balsam of Tolu essence, pine oil, and the like. Examples of naturally occurring pigments include carbon black, ocher, hematite, clay, chromium oxide, copper oxide and the like. Examples of naturally occurring dyes include indigo, litmus, curcuma, carmine, chlorophyll and walnut oil.

Bees wax is a naturally occurring solid wax derived from the honeycomb of the bee. It may be bleached bees wax (cera alba) or unbleached bees wax (cera flava) and it usually has a specific gravity of about 0.95 and melts within a range of about 62°–65°C. Natural honeycomb may be used without further processing other than removal of the honey. In instances where the bees wax is bleached, this is preferably done by natural means. Unbleached bees wax may be prepared by melting honeycomb in hot water, straining and cooling the molten wax in molds. The resultant product (cera flava) is a yellow to greyish brown solid with a honey-like odor and a faint characteristic taste. In instances where a white bees wax (cera alba) is desired, the cera flava may be bleached by sunlight or chemical oxidizing agents such as hydrogen peroxide, ozone or chromic acid to produce a white solid which is translucent in thin layers and nearly tasteless. The general properties of bleached bees wax are substantially the same as for unbleached bees wax with the exception of color, odor and taste.

Paraffin wax is a solid wax derived from petroleum and thus it is a naturally occurring product. It is a white, translucent, waxy, tasteless and odorless solid consisting of a mixture of solid hydrocarbons chiefly of the methane series. It usually has a specific gravity of about 0.880–0.914 and a melting point of about 47–65°C. Microcrystalline waxes or other waxes derived from petroleum and having similar properties may be used and are embraced by the term paraffin wax.

The hair grooming composition of the invention may be prepared by melting the bees wax and the paraffin wax and admixing the same in the above described proportions by volume. Preferably, the resultant molten ingredients are agitated sufficiently so as to assure that a homogeneous molten composition is formed. Thereafter, the molten composition is solidified in a desired shape, with or without a reinforcement, or it is applied to a suitable substrate and is solidified thereon. For example, when a solid stick, rod, bar or similar configuration of the composition is being prepared, the molten composition may be cast into a mold and solidified therein by cooling, and then removed from the mold following solidification. If desired, a reinforcing member made of a suitable reinforcing material such as metal, wood, reed, cane, textile materials, or plastic may be inserted into the molten mixture prior to solidification. Upon solidification, the reinforcement is embedded in the resultant solid composition and reinforces the same during use and reduces the likelihood of damage or breakage. Alternatively, a reinforcing substrate or other substrates such as the handles of combs, brushes and the like may be dipped into the molten composition and then removed and quickly cooled to solidify the layer of liquid composition on the substrate. The steps of dipping the substrate into the molten composition followed by rapid removal from the molten composition and cooling of the layer of liquid composition thereon may be repeated a number of times until the desired thickness of the solidified hair grooming composition is achieved.

Referring now to FIGS. 1 and 2 of the drawings, the comb generally designated as 10 comprises a handle portion 11 and teeth 12 which extend downward from supporting portion 14. A body 15 of hair grooming composition of the invention described above surrounds the handle 11 and tightly adheres thereto. The handle 11 also serves as a reinforcement for the body 15 and the diameter thereof is of a size convenient to be grasped by the hand when grooming the hair with the comb 10.

Similarly, the prior art hair brush generally designated as 16 in FIGS. 3 and 4 includes a handle 17 and a supporting portion 18 for bristles 19. A body 20 of the hair grooming composition described above surrounds the handle 17 and tightly adheres thereto. The handle 17 also serves as a reinforcement for the body 20 and the diameter thereof is such that it may be conveniently held in the hand when grooming the hair with the brush 16.

Referring now to FIGS. 5 and 6 of the drawings, the hair grooming instrument generally designated as 21 includes an elongated rod-shaped body 22 of the above described hair grooming composition and an elongated rod-shaped member 23 which has a markedly smaller diameter. The member 23 includes a reinforcing inner end 24 which is embedded in the body 22 and serves to reinforce the same, and a handle end 25 which extends outward therefrom for a distance sufficient to serve as a handle. FIGS. 7 and 8 of the drawings illustrate a somewhat similar reinforced hair grooming instrument generally designated as 26 including an elongated rod shaped body 27 of hair grooming composition which completely surrounds reinforcement 28. The length and diameter of body 27 are such that one end may be conveniently grasped and held by the hand while stroking the hair with the other end and thereby applying the hair grooming composition.

FIG. 9 of the drawing illustrates a bar generally designated as 29 of the hair grooming composition described herein. The bar 29 is shown as being unreinforced with a flower motif 30 thereon, but may be reinforced and of plain design when desired. It may be of a size for conveniently holding in the hand while applying the hair grooming composition to the hair. Preferably, one side of the bar 29 is in contact with the palm of the hand whereby it is warmed while stroking the hair with the other side. Thus, upon frequently rotating the bar in the palm of the hand, the freshly warmed surfaces may be contacted with the hair to thereby allow the application of the warmed hair grooming composition and thus improve results.

When using the comb 10 or the hair brush 16, the bodies 15 and 20, respectively, of the hair treating composition are grasped by the hand and warmed while grooming the hair with the respective instruments. After the bodies 15 and 20 are warm, the supporting portions 14 and 18 are grasped by the hand and the freshly warmed bodies 15 and 20, respectively, are contacted with the hair with a gentle stroking action to thereby apply the same. The steps of alternately grooming the hair with the comb and brush 10 and 16, and then contacting the hair with the freshly warmed bodies 15 and 20, respectively, of the hair grooming composition may be repeated at frequent intervals so as to assure that the hair grooming composition is warm at the time of application. Similarly, one end of the body 27 of instrument 26 may be grasped by the hand while contacting the other end thereof with the hair and applying the composition, followed by frequent reversing of the ends so as to assure that the freshly warmed composition is applied. When using the hair grooming instrument 21 to apply the composition, the handle 25 may be grasped in the hand and the body 22 may be intimately contacted with the hair using a stroking action. The body 22 may be prewarmed by means other than the hand when desired, or it may be applied without warming.

The proportion of bees wax to paraffin wax described herein is critical and must be followed to achieve acceptable results. In instances where too little of the bees wax is present, then the resultant composition is too hard to be conveniently applied to the hair in the form of a uniform film of sufficient thickness. When too much of the bees wax is present, then the composition is too soft and a coating of excessive thickness is applied to the hair. It is therefore apparent that the volume ratio of bees wax to paraffin wax described herein produces a hair grooming composition which has an optimum consistency. Further, this consistency results in the application of a controlled optimum amount of the composition to the hair upon stroking or otherwise intimately contacting the hair therewith. Thus, when properly practicing the method of the invention, it is impossible to apply either too much or too little of the composition to the hair. This highly unusual and unexpected result is presently thought to be due to the use of only two active ingredients in the composition, namely, the bees wax and the paraffin wax, and the carefully controlled volume-ratio thereof as described herein.

The hair grooming composition of the invention is further characterized by a number of unique and beneficial properties. For example, long free flowing hair does not tangle or knot during subsequent brushing or combing. Each individual hair is thereby coated with the composition and stands out in greater detail, and thus the hair gives the overall appearance of being much thicker and luxurious. The composition also preserves the hair and reduces surface damage thereto, and it is especially useful in preventing the formation of split ends and the propagation thereof when once formed. The hair also takes on a pleasing naturally appearing lustre and is much softer, and it may be combed or brushed with greater ease as the composition appears to lubricate the hair. Tangles initially present in the treated hair may be removed much easier by brushing or combing and the general consistency and feel of the hair is greatly improved. The hair is not greasy in feel or appearance, nor is it too dry.

FIGS. 10 and 11 of the drawings illustrate a hair grooming instrument generally designated as 31 including an elongated rod shaped body 32 of the hair grooming composition which is not reinforced. Otherwise, the unreinforced instrument 31 is similar to the reinforced instrument 26. The length and diameter of the body 32 are such that one end may be conveniently grasped and warmed by the hand while stroking the hair with the other and when applying the hair grooming composition. The ends may be reversed frequently to assure that a warmed composition is applied to the hair.

The hair grooming composition described herein is sufficiently flexible and coherent to be used without a reinforcement in many instances. The unreinforced hair grooming instruments of FIGS. 9, 10 and 11, for example, are unique in this respect. A composition containing from 85 to 95% by volume of paraffin wax would normally be expected to retain the characteristics thereof and be brittle and fragile. Nevertheless, the unreinforced hair grooming instruments of the invention are capable of withstanding normal use for the intended purpose in this respect. In instances where the hair grooming instruments are expected to receive rough or harsh treatment, then they may be reinforced as illustrated in FIGS. 1–8 of the drawings.

The foregoing detailed description and the following specific examples are for purposes of illustration only, and are not intended as being limiting to the spirit or scope of the appended claims.

EXAMPLE 1

Unbleached bees wax and paraffin wax were melted. Thereafter 10 parts by volume of the molten bees wax and 90 parts by volume of the molten paraffin were admixed in a vessel with vigorous agitation so as to form a homogeneous admixture thereof. The admixture thus prepared was used in preparing hair grooming instruments similar to those illustrated in FIGS. 1, 3, 5, 7, 9, and 10 of the drawings which included a solid body or shape of the hair grooming composition.

The resultant hair grooming instruments were tested by intimately contacting the hair therewith following a stroking action. It was found that the hair grooming composition was applied in the form of a thin, uniform, non-sticky and non-tacky film on each individual hair. This resulted in each individual hair appearing to be larger and more pronounced, and the overall head of hair was much more luxurious, lustrous and soft to the touch. It was possible to comb or brush out tangles in the hair much more easily than in the absence of the coating of the hair grooming composition. Additionally, there was a greatly reduced tendency of the hair to knot or tangle subsequent to the application of the hair grooming composition. Warming of the hair grooming composition with the hand prior to application also improved results and it was even easier to apply.

The presence of a reinforcement in the solid body of the hair grooming composition, such as the handles of the comb and brush as illustrated in FIGS. 1 and 3, and the members 23 and 25 as illustrated in FIGS. 5 and 7 markedly increased the strength. However, surprisingly the addition of the bees wax to the paraffin wax in the abovementioned amount produced a hair grooming composition which was characterized by greatly increased flexibility and strength as compared with the initial ingredients. The composition could be molded without a reinforcement in the form of a bar similar to a bar of soap as illustrated in FIG. 9, or in the form of an elongated rod as illustrated in FIG. 10.

EXAMPLE II

The general procedure of Example I was followed with the exception of varying the relative proportions of the molten bees wax and the molten paraffin wax. The ratio was varied between 5 parts by volume of molten bees wax to 95 parts by volume of molten paraffin wax and 15 parts by volume of molten bees wax to 85 parts by volume of molten paraffin wax. The hair grooming instruments prepared therefrom were tested by the general procedure of Example I and were found to be satisfactory.

Hair grooming compositions containing less than about 5 parts by volume of bees wax were extremely hard and could not be applied satisfactorily.

In instances where the bees wax content was increased above 15 parts by volume, then the composition was too soft and tacky and it could not be applied satisfactorily.

EXAMPLE III

The general procedure of Example I was repeated with the exception of using a formulation containing 100% by volume of bees wax and a formulation containing 100% by volume of household paraffin wax. The hair grooming instruments prepared from the resulting 100% bees wax and the 100% paraffin wax were tested following the general procedure of Example I and were found to be entirely unsatisfactory.

I claim:

1. A solid composition for use in grooming the hair consisting of as active ingredients about 5–15% by volume of bees wax and about 95–85% by volume of paraffin wax.

2. The composition of claim 1 wherein the said solid composition consists of as active ingredients about 10% by volume of bees wax and about 90% by volume of paraffin wax.

3. A method of grooming the hair which consists essentially of intimately contacting the hair with the said solid composition of claim 1 whereby a thin film thereof is applied to the hair.

4. A method of grooming the hair which consists essentially of intimately contacting the hair with the said solid composition of claim 2 whereby a thin film thereof is applied to the hair.

5. An instrument for grooming the hair which consists of as active ingredients a body of the said solid composition of claim 1 and a reinforcing means therefor, the said reinforcing means being effective to maintain the general integrity of the said body while applying the composition to the hair.

6. The instrument of claim 5 wherein the said body is elongated and the said reinforcing means extends longitudinally therein whereby it is effective to longitudinally reinforce the said body.

7. The instrument of claim 6 wherein the said reinforcing means extends outward past the said elongated body a distance sufficient to form a handle therefor.

8. An instrument for grooming the hair which consists essentially of hair grooming means for passing into intimate contact with the hair, handle means carried by and extending outward from the said hair grooming means, the said handle means providing a handle for grasping with the hand when grooming the hair with the said hair grooming means, and a hair grooming composition carried by the said handle means, the said hair grooming composition consisting essentially of about 5–15% by volume of bees wax and about 95–85% by volume of paraffin wax, the said hair grooming composition being positioned on the said handle means whereby it is contacted and warmed by the hand when grooming the hair with the said hair grooming means, and the said hair grooming means also constituting a secondary handle means whereby it may be grasped by the hand and the said warmed hair grooming composition passed into intimate contact with the hair to thereby apply a thin coating thereof to the hair.

9. The instrument of claim 8 wherein the said hair grooming means is a hair brush.

10. The instrument of claim 8 wherein the said hair grooming means is a comb.

* * * * *